(12) United States Patent
Vahlberg et al.

(10) Patent No.: US 9,715,671 B2
(45) Date of Patent: Jul. 25, 2017

(54) FACILITY-WIDE MEDICATION MANAGEMENT SYSTEMS

(75) Inventors: John Vahlberg, Mountain View, CA (US); Mike Dougan, Mountain View, CA (US)

(73) Assignee: Omnicell, Inc., Mountain View, CA (US)

( * ) Notice: Subject to any disclaimer, the term of this patent is extended or adjusted under 35 U.S.C. 154(b) by 526 days.

(21) Appl. No.: 13/462,789

(22) Filed: May 2, 2012

(65) Prior Publication Data

US 2013/0006652 A1    Jan. 3, 2013

Related U.S. Application Data

(60) Provisional application No. 61/481,599, filed on May 2, 2011.

(51) Int. Cl.
*G06Q 10/00* (2012.01)
*G06Q 50/00* (2012.01)
*G06Q 10/08* (2012.01)
*G06F 19/00* (2011.01)

(52) U.S. Cl.
CPC ....... *G06Q 10/087* (2013.01); *G06F 19/3462* (2013.01)

(58) Field of Classification Search
CPC ..... G06Q 50/22; G06Q 50/24; G06F 19/3462
See application file for complete search history.

(56) References Cited

U.S. PATENT DOCUMENTS

| 5,190,185 | A | 3/1993 | Blechl |
| 5,377,864 | A | 1/1995 | Blechl et al. |
| 5,468,110 | A | * 11/1995 | McDonald et al. .......... 414/273 |
| 5,745,366 | A | 4/1998 | Higham et al. |
| 5,805,455 | A | 9/1998 | Lipps |
| 5,805,456 | A | 9/1998 | Higham et al. |

(Continued)

FOREIGN PATENT DOCUMENTS

| CN | 101785021 A | 7/2010 |
| WO | 02/23459 A2 | 3/2002 |

(Continued)

OTHER PUBLICATIONS

International Search Report and Written Opinion of PCT/US12/036197 mailed on Aug. 31, 2012, 8 pages.

(Continued)

*Primary Examiner* — Elaine Gort
*Assistant Examiner* — Trang Nguyen
(74) *Attorney, Agent, or Firm* — Kilpatrick Townsend & Stockton LLP (57) ABSTRACT

A system for managing medications facilitates documentation of medication returned from remote dispensing units to a central storage location such as a pharmacy vault. The system may be especially useful in facilitating the tracking of controlled substances. The system receives an indication that a medication previously removed from the remote dispensing units has been designated for return to the medication management system. The system computes an estimated return amount of the medication, and causes a queued return list to be displayed at the central storage location. The system can accommodate multiple remote dispensing devices and multiple medications.

19 Claims, 6 Drawing Sheets

(56) References Cited

U.S. PATENT DOCUMENTS

| | | | |
|---|---|---|---|
| 5,905,653 A * | 5/1999 | Higham et al. | 700/244 |
| 5,927,540 A | 7/1999 | Godlewski | |
| 6,011,999 A | 1/2000 | Holmes | |
| 6,039,467 A | 3/2000 | Holmes | |
| 6,073,834 A * | 6/2000 | Michael et al. | 232/43.1 |
| 6,151,536 A | 11/2000 | Arnold et al. | |
| 6,170,929 B1 | 1/2001 | Wilson et al. | |
| 6,272,394 B1 | 8/2001 | Lipps | |
| 6,385,505 B1 | 5/2002 | Lipps | |
| 6,609,047 B1 | 8/2003 | Lipps | |
| 6,640,159 B2 | 10/2003 | Holmes et al. | |
| 6,760,643 B2 | 7/2004 | Lipps | |
| 6,975,922 B2 | 12/2005 | Duncan et al. | |
| 7,348,884 B2 | 3/2008 | Higham | |
| 7,349,858 B1 * | 3/2008 | McGrady et al. | 705/3 |
| 7,571,024 B2 | 8/2009 | Duncan et al. | |
| 7,675,421 B2 | 3/2010 | Higham | |
| 7,835,819 B2 | 11/2010 | Duncan et al. | |
| 8,027,749 B2 | 9/2011 | Vahlberg et al. | |
| 8,073,563 B2 | 12/2011 | Vahlberg et al. | |
| 8,126,590 B2 | 2/2012 | Vahlberg et al. | |
| 8,131,397 B2 | 3/2012 | Vahlberg et al. | |
| 8,140,186 B2 | 3/2012 | Vahlberg et al. | |
| 8,155,786 B2 | 4/2012 | Vahlberg et al. | |
| 2002/0032582 A1 | 3/2002 | Feeney, Jr. et al. | |
| 2008/0065418 A1 * | 3/2008 | Byrom et al. | 705/3 |
| 2008/0319575 A1 | 12/2008 | Vahlberg | |
| 2008/0319576 A1 | 12/2008 | Vahlberg et al. | |
| 2008/0319577 A1 * | 12/2008 | Vahlberg et al. | 700/241 |
| 2008/0319579 A1 | 12/2008 | Vahlberg et al. | |
| 2008/0319789 A1 | 12/2008 | Vahlberg et al. | |
| 2008/0319790 A1 | 12/2008 | Vahlberg et al. | |
| 2010/0042437 A1 * | 2/2010 | Levy | G06Q 10/087 705/3 |
| 2013/0024204 A1 * | 1/2013 | Hendrix et al. | 705/2 |

FOREIGN PATENT DOCUMENTS

| | | |
|---|---|---|
| WO | 2008/157632 A2 | 12/2008 |
| WO | 2009/086217 A2 | 7/2009 |
| WO | 2011/008765 A1 | 1/2011 |
| WO | 2011/049167 A1 | 4/2011 |

OTHER PUBLICATIONS

Extended European Search Report for EP12779298 Dated Aug. 13, 2014, 17 pages.

AU Patent Application No. 2012250765, "First Examination Report", dated Jul. 19, 2015, 4 pages.

CN201280033133.8, "Office Action", Mar. 21, 2016, 13 pages.

JP2014-509419, "Office Action", Jun. 28, 2016, 4 pages.

Chinese Patent Application No. CN2012833133, "Office Action" mailed on Nov. 8, 2016, 10 pages.

AU Patent Application No. 2012250765, "Second Examination Report", dated Jan. 24, 2017, 3 pages.

JP Patent Application No. 2014-509419, "Office Action", mailed on Mar. 1, 2017, 4 pages.

EP Patent Application No. 12 779 298.4, "Office Action", dated Apr. 24, 2017, 8 pages.

* cited by examiner

CONTROLLED SUBSTANCE MANAGEMENT

Queued Returns from Cabinet: 103   User: Pat Pharmatech

| | Item | Return | Dispose | Waste |
|---|---|---|---|---|
| ✓ | Acetaminophen with codeine | 1 | 0 | 0 |
| ☐ | Oxycodone | 2 | 0 | 0 |
| ☐ | Phenergan | 0 | 5 | 0 |
| ☐ | | | | |

[ ACCEPT ]   [ EDIT ]   [ CANCEL ]

QUEUED RECEIVING LIST

Items expected from: <u>ACME Meds</u>     User: Pat Pharmatech

| Item | Number expected |
|---|---|
| ☑ Methodone | 40 |
| ☐ Hydrocodone | 50 |
| ☐ Amphetamine | 10 |
| ☐ Acetaminophen with codeine | 1000 |

ACCEPT     EDIT     CANCEL

FACILITY-WIDE MEDICATION MANAGEMENT SYSTEMS

This application claims priority to U.S. Provisional Patent Application No. 61/481,599, filed May 2, 2011 and titled "Facility-Wide Medication Management Systems", the entire disclosure of which is hereby incorporated by reference herein for all purposes.

BACKGROUND OF THE INVENTION

Medical facilities employ a wide variety of medical items, including medical supply items, pharmaceuticals, and the like. These items are used in a variety of locations, such as operating rooms, patient recovery rooms, labor and delivery rooms, and storage areas, such as secure vaults, dispensing cabinets and the like. Healthcare facilities have a need to track and account for items in an efficient manner. In some cases, for example in the case of supplies such as bandages, tape, and the like, the tracking may be performed primarily for inventory and billing purposes. However, for many medical items such as pharmaceuticals, and especially for legally controlled substances, it is important to carefully track the movement and disposition of the items throughout the facility.

The accurate and timely tracking of controlled substances depends on the accurate input of information by facility personnel indicating when items are moved throughout the system. There is a need to facilitate the efficient entry of accurate tracking information by health care workers.

BRIEF SUMMARY OF THE INVENTION

According to one aspect, a medication management system includes an electronic network a computer system. The computer system is programmed to receive over the electronic network one or more indications that a particular medication previously removed from a dispensing device has been designated for return to the medication management system. The computer system computes an estimated return amount that is an amount of the previously-removed particular medication that is estimated to be returned to a central storage location within the medication management system. The computer system also causes a queued return list of one or more estimated return amounts to be displayed at the central storage location to facilitate documentation of the return of the particular medication to the central storage location.

DETAILED DESCRIPTION OF THE INVENTION

Figure 1:
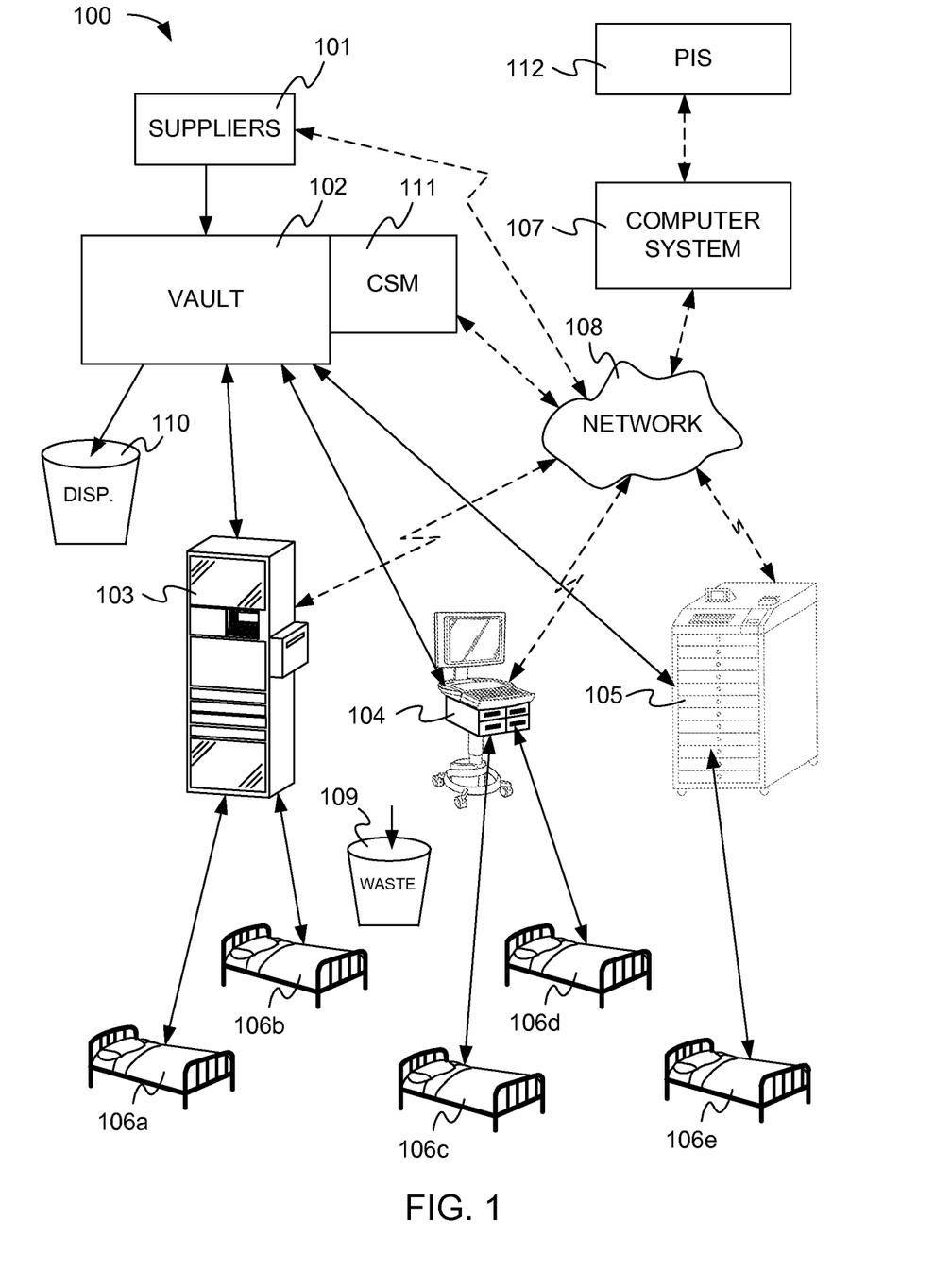
FIG. 1 illustrates a medication management system in accordance with an embodiment of the invention.

FIG. 1 illustrates a medication management system 100 in accordance with an embodiment of the invention. System 100 may be, for example, within a hospital or other health care facility. System 100 will be explained primarily in the context of tracking and accounting for controlled substances, but it will be recognized that embodiments of the invention may be used for other purposes.

A controlled substance is typically any medication or other substance whose use and possession is subject to government regulation. In the United States, controlled substances are assigned to different schedules depending on their potential for abuse and their applicability for medical use. Schedule I drugs have a high potential for abuse and have no currently acceptable medical use, and are not typically found in a hospital setting. Examples of schedule I drugs include heroin and LSD. Drugs in Schedules II-V have important medical uses and varying degrees of potential for abuse. Examples of medications assigned to Schedule II include narcotics such as morphine and oxycodone, and stimulants such as methamphetamine. At the other end of the spectrum, examples of Schedule V substances include cough suppressants having limited amounts of codeine.

Government regulations require healthcare facilities to track and account for controlled substances in order to discourage and detect diversion of these substances to illicit use. System 100 is designed to provide the required accounting and tracking.

In system 100, controlled substances flow into the system from suppliers 101, and may leave the system in various ways. Typically, upon receipt, the substances are stored in a central storage location such as vault 102. Vault 102 may reside in a hospital's pharmacy, and may include physical security features such as locks and computerized access controls that limit access only to certain personnel. Vault 102 may take any of a number of forms, and may include, for example, open storage such as shelves, a refrigerator, a cabinet as described in more detail below, other storage devices, or any combination of these. Vault 102 may be enclosed in a separate lockable room.

From vault 102, medications may be stocked into remote dispensing devices such as cabinet 103, cart 104, and movable cabinet 105. For example, the remote dispensing devices may be located in specific wards or floors of the healthcare facility, and provide convenient access to patient medications for floor personnel. These devices may include one or more locking doors, drawers, or the like, which may further contain storage locations such as compartments, drawers, or bins for storing individual medications. Some storage locations may be for general use, and store only single medication, while other storage locations may be patient-specific, such that they hold medications for the use of a single patient. Patient-specific storage locations may be compartments, drawers, bins, or other kinds of locations, for example the kinds of bins described in the patents and patent applications previously incorporated by reference. Patient specific locations may hold more than one kind of medication. The system may utilize specialized dispensing devices in some locations, for example a dispensing device specially adapted for use in anesthesiology.

Stocking of medications from vault 102 to the dispensing devices 103-105 may be the responsibility of pharmacy personnel. For example, a pharmacy technician may periodically service each dispensing device, restocking medications into the dispensing devices, and performing other tasks as described in more detail below.

A nurse or other healthcare worker can then access the remote storage devices to obtain medication to be dispensed to patients in beds 106a-106e. Access to the remote dispensing devices may also be controlled. For example, a nurse or other healthcare worker removing any medication may be required to provide an identification each time he or she accesses the device, and may also be required to indicate what medication is being removed and which patient the medication is to be administered to. The remote dispensing device may then open only the drawer or door that provides access to that medication, and may visually indicate which bin contains the medication, for example by flashing a light adjacent the correct bin.

In FIG. 1, flows of medications are shown using solid arrows.

It will be recognized that cabinet 103, cart 104, and movable cabinet 105 are examples of remote dispensing devices, and that dispensing devices of other configurations may be used. Other example dispensing devices are described in the following commonly owned U.S. Patents and patent applications, the contents of which are hereby incorporated by reference: U.S. Pat. No. 6,272,394, issued on Aug. 7, 2001 to Lipps, U.S. Pat. No. 6,385,505, issued on May 7, 2002 to Lipps, U.S. Pat. No. 6,760,643, issued on Jul. 6, 2004 to Lipps, U.S. Pat. No. 5,805,455, issued on Sep. 8, 1998 to Lipps, U.S. Pat. No. 6,609,047, issued on Aug. 19, 2003 to Lipps, U.S. Pat. No. 5,805,456, issued on Sep. 8, 1998 to Higham et al, U.S. Pat. No. 5,745,366, issued on Apr. 28, 1998 to Higham et al., an U.S. Pat. No. 5,905,653, issued on May 18, 1999 to Higham et al., U.S. Pat. No. 5,927,540, issued on Jul. 27, 1999 to Godlewski, U.S. Pat. No. 6,039,467, issued on Mar. 21, 2000 to Holmes, U.S. Pat. No. 6,640,159, issued on Oct. 28, 2003 to Holmes et al., U.S. Pat. No. 6,151,536, issued on Nov. 21, 2000 to Arnold et al., U.S. Pat. No. 5,377,864, issued on Jan. 3, 1995 to Blechl et al., U.S. Pat. No. 5,190,185, issued on Mar. 2, 1993 to Blechl, U.S. Pat. No. 6,975,922, issued on Dec. 13, 2005 to Duncan et al., U.S. Pat. No. 7,571,024, issued on Aug. 4, 2009 to Duncan et al., U.S. Pat. No. 7,835,819, issued on Nov. 16, 2010 to Duncan et al., U.S. Pat. No. 6,011,999, issued on Jan. 4, 2000 to Holmes, U.S. Pat. No. 7,348,884, issued on Mar. 25, 2008 to Higham, U.S. Pat. No. 7,675,421, issued on Mar. 9, 2010 to Higham, U.S. Pat. No. 6,170,929, issued on Jan. 9, 2001 to Wilson et al., U.S. Pat. No. 8,155,786 to Vahlberg et al., issued on Apr. 10, 2012, U.S. Pat. No. 8,073,563 to Vahlberg et al., issued on Dec. 6, 2011, U.S. Patent Application Publication No. 2008/0319577 of Vahlberg et al., published on Dec. 25, 2008, U.S. Pat. No. 8,140,186 to Vahlberg et al., issued on Mar. 20, 2012, U.S. Pat. No. 8,126,590 to Vahlberg et al., issued on Feb. 28, 2012, U.S. Pat. No. 8,027,749 to Vahlberg et al., issued on Sep. 27, 2011, U.S. Patent Application Publication No. 2008/0319790 of Vahlberg et al., published on Dec. 25, 2008, U.S. Patent Application Publication No. 2008/0319789 of Vahlberg et al., published on Dec. 25, 2008, U.S. Pat. No. 8,131,397 to Vahlberg et al., issued on Mar. 6, 2012, U.S. Patent Application Publication No. 2008/0319579 of Vahlberg et al., published on Dec. 25, 2008, and U.S. Patent Application Publication No. 2010/0042437 of Levy et al., published on Feb. 18, 2010.

The remote dispensing devices are preferably in electronic communication with a central computer system 107 via network 108. Network 108 may be any suitable network, for example, a facility-wide electronic network, and may be wired, wireless, or a combination thereof. Information flows are shown in FIG. 1 using dashed arrows. Network 108 may also connect directly or indirectly to outside entities, such as suppliers 101.

Central computer system 107 may maintain detailed records of the locations of all medications in the system, and receives a notification each time the vault or one of remote dispensing devices is accessed by a nurse, technician, or other worker. The notification may include the identity of the person who has accessed the dispensing device, the medication involved, and what kind of transaction was performed, as is discussed in more detail below. Central computer system 107 may be, for example, a server such as an OmniCenter® server, available from Omnicell, Inc. of Mountain View, Calif., USA. Central computer system 107 may communication with other systems within the facility, for example pharmacy information system 112 to receive patient admission, transfer, and discharge information, patient medication orders, and the like. In other embodiments, a computer system that performs functions of the invention need not be a centralized computer system, so long as it has access to sufficient information to perform the functions of the invention. While only a single block is used to indicate computer system 107 in FIG. 1, computer system 107 may include multiple computers that may be collocated or widely distributed.

Ideally, medications leave the system in only three ways. In a first way, medication is administered to a patient. In a second way of leaving the system, medication may be wasted. For example, if the medication is packaged in a quantity that exceeds the prescribed dose for a particular patient, each administration may result in a leftover amount that is not reusable, and must be discarded 109. In another example of waste, a vial may be dropped and broken, rendering its contents unusable. In a third way of leaving the system, medication may be returned to vault 102 for disposal in a controlled manner 110, for example because the medication has reached its expiration date.

However, controlled substances can also leave the system in other ways, for example due to inadvertent mistake, but also intentionally for illicit use or sale. The illicit removal of controlled substances is known in the art as diversion. In order to discourage and detect diversion, every movement of a controlled substance between vault 102 and dispensing devices 103-105 may be carefully tracked, and an inventory of every controlled substance within vault 102 and dispensing devices 103-105 is kept by a controlled substance management system (CSM) 111. CSM 111 may be, for example, a dedicated computer system that tracks the controlled substance inventory and communicates via network 108 with central computer system 107. As central computer system 107 receives indications of the movements of medications, supplies, and other items throughout system 100, it recognizes that certain transactions involve controlled substances, and notifies CSM 111. For example, if a nurse removes a quantity of a controlled substance from cart 104 for administration to a patient, the nurse inputs details of that transaction into cart 104, which in turn sends the transaction details to central computer system 107. Central computer system 107 recognizes that this transaction affects the facility's inventory of controlled substances, and informs CSM 111, which can update its records accordingly. Central computer system 107 may also inform CSM 111 of individual patient medication orders and the locations of patient-specific bins or other locations within the system. CSM 111 can then facilitate management of patient medications as explained in more detail below.

CSM 111 may monitor transactions involving controlled substances for discrepancies that may indicate errors or diversion. For example, if a technician removes a quantity of medication from vault 102 for stocking in one of dispensing devices 103-105, but a different quantity is actually stocked in the intended dispensing device, CSM 111 may flag the discrepancy for further investigation. Accurate tracking of the flow of controlled substances depends on timely and accurate data entry at all points in the system.

In one aspect, embodiments of the invention facilitate efficient documentation of returns of medication to vault 102.

Returns may occur for a variety of reasons. In a typical scenario, a nurse may dispense one dose of acetaminophen with codeine from cabinet 103 for administration to a patient in bed 106b. The nurse enters the details of this transaction into cabinet 103, which communicates them to central computer system 107. Central computer system 107 recognizes that this transaction affects the facility's inventory of controlled substances, and informs CSM 111, which can update its records to reflect the fact that the removed medication has left the CSM system and is therefore no longer in the CSM inventory. (The medication may be subject to further tracking outside of CSM 111, for example the nurse may be required to document what quantity was actually administered to the patient, and may be required to have any waste of medication witnessed by another person.)

However, not all of the medication may be administered to the patient. For example, the patient may decline to take any pain medication at the time, or the patient may be discharged in the interim. In this kind of situation, some or all of the medication may need to be returned to the system. The return must be accounted for, and the medication recognized as being once again in the controlled substance inventory.

Figure 2:
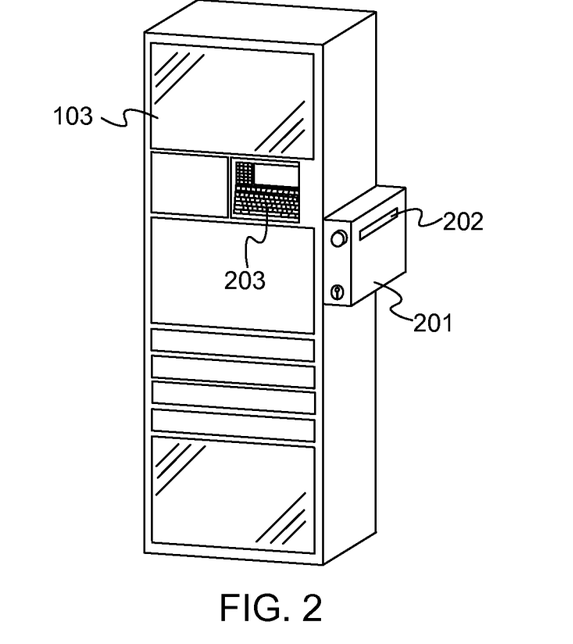
FIG. 2 illustrates an enlarged view of a cabinet in the system of FIG. 1.

FIG. 2 illustrates an enlarged view of cabinet 103, and shows a return bin 201 attached to cabinet 103. The nurse typically is not authorized to return medication to bins within cabinet 103 itself. Rather, the nurse places the unused acetaminophen with codeine into return bin 201, and the medication is then handled at a later time by a pharmacy technician or other person having responsibility for controlled substance management.

Return bin 201 may be a secure, lockable compartment with a limited access opening 202, through which items can be deposited in return bin 201, but through which it is difficult or impossible to remove items without a key or other access mechanism. For example return bin 201 may include a rotating mechanism into which items can be placed through slot 202, and which can be rotated to drop the items into return bin 201, but which then blocks access to the interior of return bin 201. Other mechanisms could be used as well.

In conjunction with placing returned medication into return bin 201, the nurse enters information about the return, for example using keyboard 203. The information includes such items as the nurse's identity, and the type and quantity of the medication returned. Cabinet 103 forwards the details of the return to central computer system 107.

At a later time, the pharmacy technician may service cabinet 103, restocking bins in cabinet 103 with medications brought from vault 102, and the like. As part of the service process, the pharmacy technician empties return bin 201. The pharmacy technician also enters details of all of the transactions performed, including the fact that return bin 201 has been emptied. These details are forwarded to computer system 107, which in turn informs CSM 111 of any transactions involving controlled substances. CSM 111 thus becomes aware of the controlled medication designated for return. In other embodiments, CSM 111 may have been informed of the pending return when the nurse first deposited the medication in return bin 201.

In previous systems, when the pharmacy technician completed his or her rounds to the remote dispensing devices 103-105 and returned to vault 102, processing the returned items involved keying in information about each item to document its return to vault 102. The process was time consuming, and presented an opportunity for error. Even in a menu-based system, the technician needed to select the medication being returned from a menu of potentially hundreds of medications, specify the dispensing device at which the medication was found and designated for return, and indicate the quantity of medication. When returning a large number of medications even these steps were very time consuming, and subject to data entry errors.

According to one aspect of the invention, system 100 computes, based on the return transaction information forwarded from the various remote dispensing devices 103-105, an amount of medication that is estimated to be returned to vault 102, and presents a queued list of estimated potential returns at CSM 111. For many returns, the pharmacy technician then need only verify that the queued return transaction is correct and indicate such to CSM 111, place the returned medication into vault 102, and document the transfer. This process is much faster and less prone to error than the manual entry used in past systems. Even when the queued return quantity is does not match the quantity that is actually returned, the technician can edit the list easily to indicate the correct returns and quantities, and the process is still efficient.

In the simple example described above, the nurse placed an unused dose of acetaminophen with codeine into return bin 201, and indicated at cabinet 103 that this had been done. Central computer system 107 recorded this event. At a later time, the pharmacy technician removes the medication from return bin 201 and indicates at cabinet 103 that he or she has done so. Cabinet 103 informs central computer system 107, which in turn informs CSM 111. In this simple case, in the absence of any other activity, CSM 111 can expect that the technician will eventually bring all of that medication from return bin 201 back to vault 102 for return to inventory.

Figure 3:
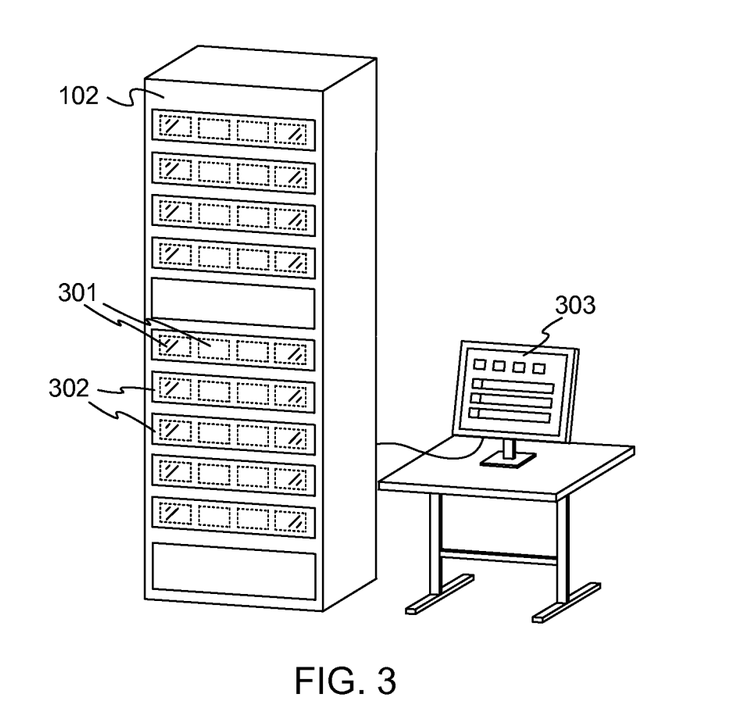
FIG. 3 illustrates an embodiment of a vault of the system of FIG. 1.

FIG. 3 illustrates an embodiment of vault 102. In this example, vault 102 may be a cabinet with characteristics similar to cabinet 103, for example a set of drawers 301 with bins 302 for holding medications. The particular configuration shown in FIG. 3 is by way of example only, and vault 102 may have any suitable configuration. For example, a vault in a large facility may include several cabinets. Vault 102 may interact with central computer system 107 in a way similar to the dispensing devices, so that access to vault 102 is controlled, and a user is guided to correct bins when adding or removing medications or other items.

A terminal 303 is provided for interacting with CSM 111. (The computer system running CSM 111 is not shown in FIG. 3.) Terminal 303 may conveniently be a touchscreen terminal, but other kinds of terminals may be used, for example a separate keyboard and display. In other embodiments, the function of terminal 303 may be built into a cabinet comprised in vault 102.

Figure 4:
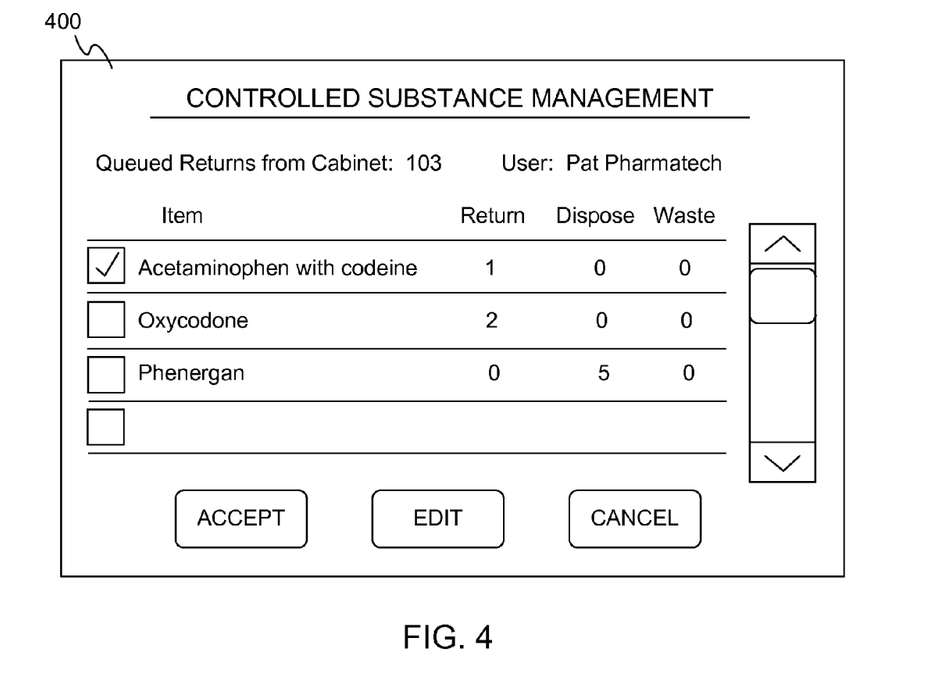
FIG. 4 illustrates an example user interface.

When the pharmacy technician arrives at vault 102 and logs in, he or she is presented with a list of items that CSM 111 has estimated will be returned. FIG. 4 illustrates an example user interface 400 that may be presented on terminal 303. It will be understood that user interface 400 is presented by way of example only, and that many other user interface configurations may be used. In this simple example, CSM 111 can easily infer that the one dose of acetaminophen with codeine removed from cabinet 103 is expected to be returned. The pharmacy technician can simply indicate that the list is correct, for example by touching "ACCEPT", and will then be guided to place the dose in the correct bin of vault 102. CSM 111 can then update its records to reflect that the dose is now in vault 102.

Similar queued return lists may be presented for medications being returned from other dispensing devices. Each queued return list may also be specific to the particular technician performing the returns.

The list presented in user interface 400 may be fully editable. For example, if the pharmacy technician notices that the dose queued for return is expired, he or she may simply edit the list to indicate that the dose is to be routed for disposal, rather than placed in vault 102. The technician may then be guided to place the item in the disposal location, and CSM 111 can account for the item as pending for disposal, rather than in vault 102. Similarly, if the item is dropped and damaged between cabinet 103 and vault 102, the technician may edit the list in user interface 400 to indicate that the item should be wasted. He or she would then be guided to place the item in a location for wasted items, rather than in vault 102, and CSM 111 can update its records accordingly. For any movement of medication done at the pharmacy, CSM 111 may also inform central computer system 107 of the transactions.

In a slightly more complex example, return bin 201 contains three units of a controlled substance, previously placed there and documented by nurses. When the nurses logged the returns at cabinet 103, cabinet 103 notified computer system 107. When the pharmacy technician later empties return bin 201, cabinet 103 notifies computer system 107, which in turn notifies CSM 111, that three units of a controlled substance have been removed from return bin 201 by the pharmacy technician. CSM 111 would then count three units as being estimated for return to vault 102. However, in this example, the technician then uses one of the units to replenish a bin holding that medication within cabinet 103, as part of his or her normal restocking procedure. That transaction is also logged by cabinet 103, and details are forwarded to computer system 107, which then informs CSM 111. CSM 111 may then decrement the number of items estimated for return, on the assumption that the technician used one of the three items from the return bin to perform the restock. The net result is that CSM will estimate that two of that item to be returned from cabinet 103 by that technician. This example may be represented as follows:

| Time | Cabinet | User | Action | Qty |
| --- | --- | --- | --- | --- |
| 8:00 | 103 | Pat | Empty Return Bin | 3 |
| 8:05 | 103 | Pat | Restock | 1 |
|  |  |  | Estimated return amount | 2 |

Yet another example may be represented as follows:

| Time | Cabinet | User | Action | Qty |
| --- | --- | --- | --- | --- |
| 8:00 | 103 | Pat | Empty Return Bin | 2 |
| 8:05 | 105 | Pat | Restock | 2 |
|  |  |  | Estimated return amount | 2 |

This example is similar to the previous example, except that instead of restocking items back into the same cabinet, the restock transaction occurs at a different cabinet. In this example, return bin 201 of cabinet 103 holds two of a particular controlled item, previously placed there and logged to the system. At the beginning of this scenario, computer system 107 is aware of the two items. When the pharmacy technician removes the items, cabinet 103 informs computer system 107, which in turn notifies CSM 111 because a controlled substance is involved. CSM 111 may then count two items as being estimated for return from cabinet 103. Later, the technician restocks two of the same item into cabinet 105. Cabinet 105 informs computer system 107, which in turn notifies CSM 111. CSM 111 may handle this situation in different ways, in different embodiments. A first option is to assume that the two items restocked into cabinet 105 are the same two items that were removed from return bin 201, and to therefore decrement the number of items estimated to be returned to zero. In this case, CSM 111 would not present that particular item in the queued returns list when the technician arrives back at vault 102. A second option is to assume that, because of the time and distance separating the two transactions, the items stocked into cabinet 105 are not the same items removed from return bin 201, and therefore to not decrement the estimated number of items to return. In that case, CSM 111 still would anticipate two returned items, and would present two of that particular item in the queued return list.

Either option may be used, even though they give different estimates of the return amount. The inventory maintained by CSM 111 is based entirely on the actual documented movements of items into and out of dispensing devices 103-105, and into and out of vault 102. Even if the queued return list shown in user interface 400 does not accurately reflect the actual number of items to be returned, the inventory is still kept correctly because the inventory tracking does not rely on the queued returns list. The purpose of the list is for convenient data entry, and it is not used for inventory tracking. For this reason, it may be preferable to make the assumption that the two items stocked into cabinet 105 are not the same items that were removed from return bin 201, and to present a list showing two items as being expected back at vault 102. If the assumption is correct, the technician can simply accept the list entry corresponding to the two items and proceed with the restock transactions. If the assumption is incorrect, the technician can simply delete the entry from the list, change the quantity to zero, or otherwise indicate that no items are to be returned. In either case, whether the assumption was correct or incorrect, very little effort is required.

However, if it were assumed that the two items were the same, CSM 111 would not present a queued return list for that item. If this assumption is correct, the technician need not do anything with regard to this item back at vault 102. However, if the assumption is incorrect, the technician will be in possession of two items to be returned, but the items will not appear on the queued return list. In this case, the technician will be required to manually inform CSM 111 that he or she has items to return, select the items from an extended list, indicate which cabinet they came from, and indicate the quantity to be returned. The burden of an incorrect assumption is much higher for the second option than the first, while the benefit of a correct assumption is comparable. For this reason, the system may be programmed to, when in doubt, make assumptions that tend to overestimate the number of entries on the queued return list. In some embodiments, CSM 111 may simply assume that all items removed from return bins will be returned to vault 102, and may present all of the items on the queued return list, regardless of any other transactions. In this way, it can be assured that the pharmacy technician will not need to perform manual data entry for returning any item, although this broad assumption may require the technician to delete many queued return entries that could have been avoided using other assumptions about item flow.

In system 100, CSM 111 includes a separate computer dedicated to controlled substance tracking CSM 111 is tightly integrated with other parts of the system, for example central computer system 107. Central computer system 107, in conjunction with computer-enabled dispensing devices 103-105, is already configured to track the movements of a variety of medications and other items throughout system 100. Because central computer system 107 informs CSM 111 of transactions involving controlled substances, CSM 111 has the information necessary to prepare the queued item return list of FIG. 4.

Figure 5:
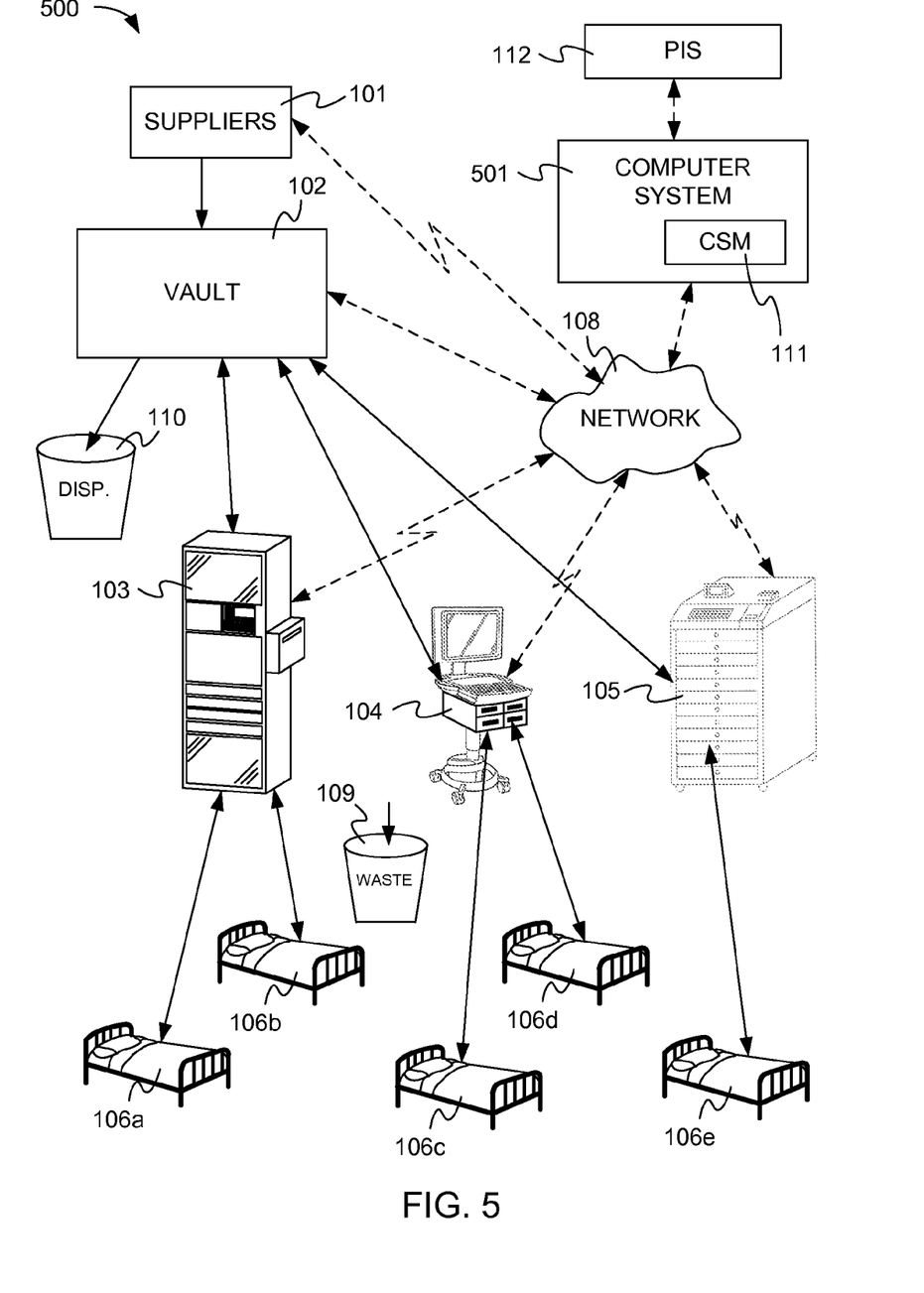
FIG. 5 illustrates a system in accordance with another embodiment of the invention.

In other embodiments, even further integration is possible. FIG. 5 illustrates a system 500 in accordance with one such embodiment. In this embodiment, central computer system 501 performs the functions of both central computer system 107 and CSM 111. Vault 102 may appear as a specialized cabinet similar to dispensing units 103-105, but for which special accounting procedures are required because vault 102 contains controlled substances.

The extensive integration of system 100 provides benefits in the tracking of medications and in the facilitation of patient care. For example, because CSM 111 is made aware of transactions involving controlled substances that occur at dispensing devices 103-105 and other locations in the system, the reach of CSM 111 to track medications throughout the facility is increased as compared with a system that is not so highly integrated, and more detail is provided that is useful for medication tracking Patient care and safety is improved, in part because manual data entry is reduced. The efficient documentation of medication transactions may result in more efficient overall movement of medications throughout the facility, so that medications are more likely to be in place when needed by patients.

In some embodiments, CSM 111 and computer system 107 may share a database of medication locations. When only a single database is used, discrepancies cannot arise between multiple databases. Integration of the system also facilitates the handling and tracking of controlled substances stored in patient-specific storage locations, as described in more detail below. Generally, in a highly integrated system, more transaction points can be monitored, and more kinds of medication movement can be tracked than in a less integrated system.

Figure 6:
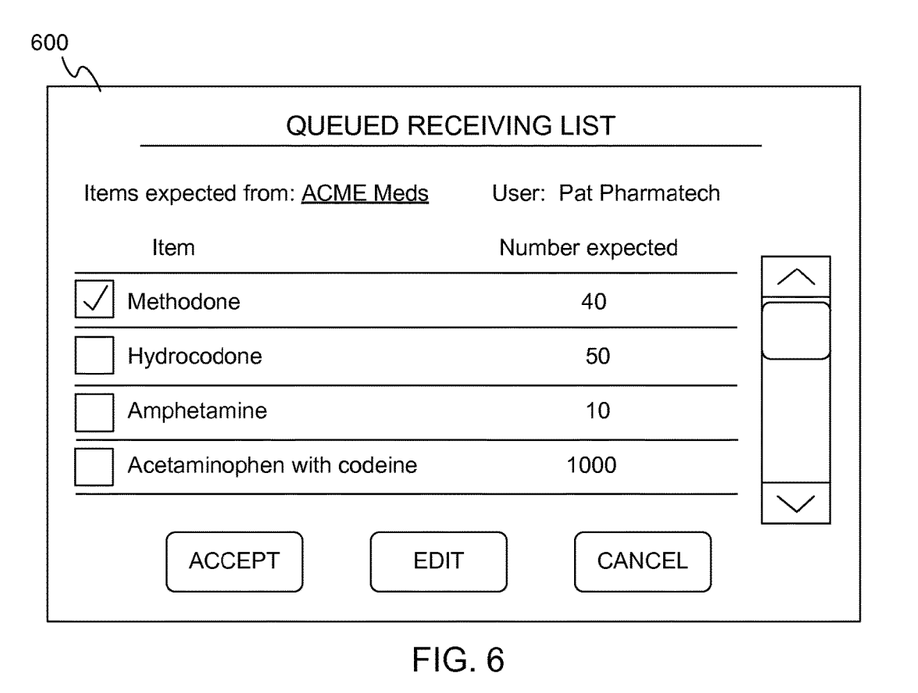
FIG. 6 illustrates an example of a queued receiving list.

In one example of integration, computer system 107 may communicate with systems located at suppliers 101. Orders for medication can be entered electronically, and suppliers 101 can provide advance shipping notice of items being shipped to the health care facility. This advance shipping notice can be used in a way similar to the queued return list shown in FIG. 4. For example, computer system 107 may identify which items on the advance shipping notice from a supplier are controlled substances, and forward a list to CSM 111 detailing which controlled substances are expected to be delivered to the health care facility from that supplier. CSM 111 can then provide a queued receiving list to assist a pharmacy technician in documenting the receipt of new shipments. An example of a queued receiving list 600 is shown in FIG. 6. A user of the system can use queued receiving list 600 in a way similar to queued return list 400. As items are removed from a received shipping container for stocking in vault 102, the technician can locate each item on queued receiving list 600 and compare the received quantity with the expected quantity. If the quantities match, the user can simply accept the list entry for that item, and proceed to stock the item into vault 102, preferably under guidance from the system. If the quantities do not match, the user can edit a list entry to reflect the amount actually received, and proceed to stock the item. The discrepancy may later appear on an exception report that triggers an investigation of the source of the discrepancy. The provision of the queued receiving list avoids laborious and error-prone manual entry of received items.

Figure 7:
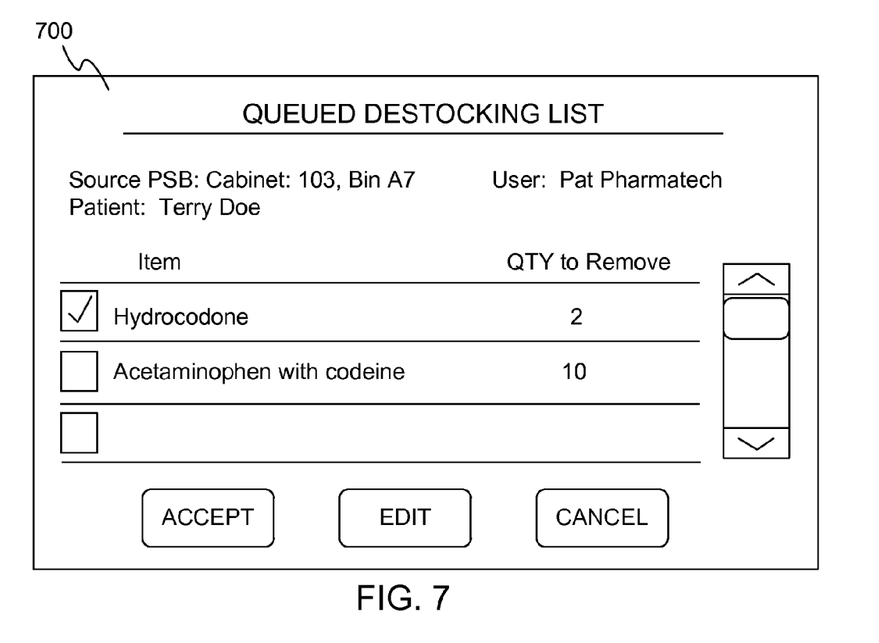
FIG. 7 illustrates and example of a queued destocking list.
Figure 8:
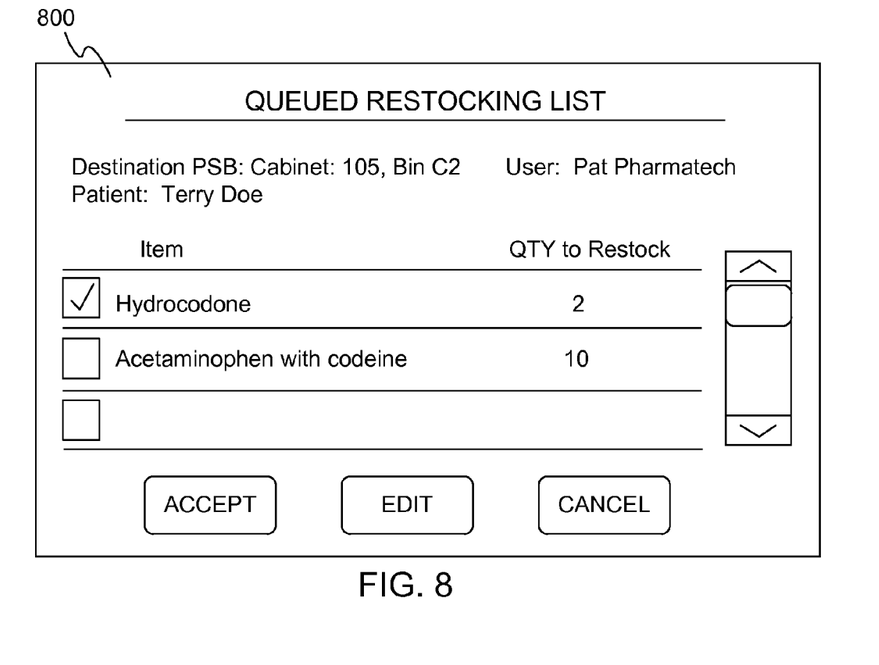
FIG. 8 illustrates an example of a queued restocking list.

In another example of integration, computer system 107 may be aware of medication orders, by virtue of its communication with pharmacy information system 112, and designates specific bins or other locations for storing medications intended for particular patients. It is common for a patient to be moved from one area of a health care facility to another. In this situation, the specific location designated for storing medication for the patient may change to another dispensing device in another area of the facility. In order to maintain continuity of patient care, it is desirable that the patient's medications also move quickly and accurately to the dispensing device in the new location. In an example of this situation, computer system 107 learns of the transfer from pharmacy information system 112, and notifies CSM 111 of the transfer. The system may then cause a queued destocking list to be displayed at the dispensing device from which the patient's medication is being moved, so that a technician removing the medication from the can document its removal by simply accepting the entries on the queued destocking list. The dispensing device may guide the technician to the correct bin from which to remove the medication being transferred. The system can then cause a queued restocking list to be displayed at the destination dispensing device, so that the technician placing the medication in the destination dispensing device can document the restocking by simply accepting entries on the queued restocking list. The destination dispensing device may guide the technician to the correct patient-specific location into which the medication is to be deposited. Examples of a queued destocking list 700 and a queued restocking list 800 are shown in FIGS. 7 and 8 respectively. For each transaction, the respective dispensing device informs computer system 107 of the transaction, and computer system 107 informs CSM 111 of any transactions involving controlled substances, so that CSM 111 can accurately track the locations of controlled substances in the system. Any discrepancies in quantities destocked and restocked may be identified for investigation, but in any event, the queued lists greatly facilitate the entry of data needed for documentation of the transfer.

In another example of integration, transactions involving movement of medication from vault 102 to dispensing devices 103-105 may also be facilitated using queued lists. For example, computer system 107 may learn of a new prescription of a controlled medication for a particular patient. In some embodiments, the patient's medications are stored in a patient-specific location. Computer system 107 informs CSM 111 of the need to move a quantity of the prescribed medication to a dispensing device near the patient. The system may cause a queued pick list to be displayed at vault 102 to facilitate documentation of picking the prescribed medication from vault 102. The system may also cause a queued stocking list to be displayed at the destination dispensing device, to facilitate documentation of the stocking of the medication into the destination dispensing device. The queued pick and stocking lists may be similar to queued destocking and restocking lists 700 and 800, although this is not a requirement. Queued pick and stocking lists may be used for medications stored in non-patient-specific locations as well.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. The invention has now been described in detail for the purposes of clarity and understanding. However, those skilled in the art will appreciate that certain changes and modifications may be practiced within the scope of the appended claims.

What is claimed is:

1. A medication management system, comprising:
an electronic network;
one or more remote medication dispensing devices coupled to the electronic network;
a display screen; and
a computer system programmed to:
receive over the electronic network from the one or more remote medication dispensing devices one or more indications that a particular medication previously removed from a dispensing device has been designated for return to the medication management system;
compute an estimated return amount that is an amount of the previously-removed particular medication that is estimated to be returned to a central storage location within the medication management system, wherein the computation of an estimated return amount is based on assumptions that tend to cause overestimation of a number of entries in a queued return list; and
cause the queued return list of one or more estimated return amounts to be displayed on the display screen at the central storage location to facilitate documentation of the return of the particular medication to the central storage location, wherein the queued return list is editable in response to inputs from a user of the system at the central storage location to modify the number of entries on the list.

2. The medication management system of claim 1, further comprising the central storage location.

3. The medication management system of claim 1, wherein the estimated return amount includes the total of all amounts of the particular medication designated for return to the medication management system from the dispensing device.

4. The medication management system of claim 1, wherein the estimated return amount is less than the total of all amounts of the particular medication designated for return to the medication management system from the dispensing device.

5. The medication management system of claim 1, wherein the computer system is programmed to:
receive indications that multiple medications previously removed from the dispensing device have been designated for return to the medication management system;
compute estimated return amounts for each of at least two of the multiple medications; and
include the at least two of the multiple medications in the queued return list.

6. The medication management system of claim 1, wherein the dispensing device is one of a plurality of dispensing devices, and wherein a respective queued return list is displayed for each of at least two of the dispensing devices from which medication is estimated to be returned.

7. The medication management system of claim 1, wherein the medication is a controlled substance.

8. The medication management system of claim 7, wherein:
the medication management system is in communication with a central computer system;
the central computer system is in communication with the dispensing device;
the dispensing device informs the central computer system of transactions involving medications occurring at the dispensing device;
the central computer system recognizes that certain transactions reported by the dispensing device involve controlled substances and informs the medication management system of the transactions involving controlled substances.

9. The medication management system of claim 1, further comprising the dispensing device.

10. The medication management system of claim 9, wherein the dispensing device is one of a plurality of dispensing devices comprised in the medication management system.

11. The medication management system of claim 1, wherein the computer system is further programmed to, upon acceptance of an entry in the queued return list by a user of the system:
guide the user to place the returned quantity of the medication described in the accepted entry into a particular bin in the central storage location; and
make a record of the return of the medication described in the entry.

12. The medication management system of claim 1, wherein the queued return list indicates an amount of an item to be disposed of.

13. The medication management system of claim 1, wherein the queued return list indicates an amount of an item to be wasted.

14. A method: of managing: medications, the method comprising:
receiving, by a computer system over an electronic network from one or more remote medication dispensing devices, an indication that a medication previously removed front a dispensing device has been designated for return to a medication management system:
computing an estimated return amount that is an amount of the previously-removed medication that is estimated to be returned to a central storage location within the medication management system, wherein the computation of the estimated return amount is based on assumptions that tend to cause overestimation of a number of entries in a queued return list;
causing the queued return list of one or more estimated return amounts to be displayed on a display screen at the central storage location to facilitate documentation of the return of the medication to the central storage location; and
altering the queued return list in response to inputs from a user of the system to modify the number of entries on the queued return list.

15. The method of claim 14, wherein computing the estimated return amount comprises computing the total of all amounts of the particular medication designated for return to the medication management system from the dispensing device.

16. The method of claim 14, wherein the method comprises:
receiving indications that multiple medications previously removed from the dispensing device have been designated for return to the medication management system;

computing estimated return amounts for at least two of the multiple medications, wherein the estimate return amounts are amounts of the previously-removed medications estimated to be returned to the central storage location; and including the at least two of the multiple medications in the queued return list.

17. The method of claim 14, wherein the dispensing device is one of a plurality of dispensing devices, and wherein the method comprises displaying a respective queued return list for each of at least two of the dispensing devices from which medication is estimated to be returned.

18. The method of claim 14, wherein the medication is a controlled substance.

19. The hod of claim 14, further comprising, upon receipt of an approval of an entry on the queued return from a user:

guiding the user to place the returned quantity of the medication described in the entry into a particular bin in the central storage location; and making a record of the return of the medication described in the entry.

\* \* \* \* \*

UNITED STATES PATENT AND TRADEMARK OFFICE
CERTIFICATE OF CORRECTION

PATENT NO. : 9,715,671 B2
APPLICATION NO. : 13/462789
DATED : July 25, 2017
INVENTOR(S) : John Vahlberg et al.

It is certified that error appears in the above-identified patent and that said Letters Patent is hereby corrected as shown below:

Column 11, Line 28, Claim 1, after computation of, please remove "an" and enter --the--.
Column 12, Line 36, Claim 14, after A method please remove ":".
Column 12, Line 36, Claim 14, after of managing please remove ":".
Column 12, Line 41, Claim 14, after removed please remove "front" and enter --from--.
Column 12, Line 42, Claim 14, after management system please remove ":" and enter --;--.
Column 13, Line 15, Claim 19, after The please remove "hod" and enter --method--.
Column 13, Line 16, Claim 19, after return please enter --list--.

Signed and Sealed this
Tenth Day of April, 2018

Andrei Iancu
*Director of the United States Patent and Trademark Office*